(12) United States Patent
Tomono

(10) Patent No.: US 9,063,130 B2
(45) Date of Patent: Jun. 23, 2015

(54) NUCLEIC ACID DETECTION METHOD AND NUCLEIC ACID DETECTION KIT

(75) Inventor: Jun Tomono, Takasago (JP)

(73) Assignee: KANEKA CORPORATION, Osaka (JP)

( * ) Notice: Subject to any disclaimer, the term of this patent is extended or adjusted under 35 U.S.C. 154(b) by 920 days.

(21) Appl. No.: 12/677,189

(22) PCT Filed: Aug. 27, 2008

(86) PCT No.: PCT/JP2008/065307
§ 371 (c)(1),
(2), (4) Date: Mar. 9, 2010

(87) PCT Pub. No.: WO2009/034842
PCT Pub. Date: Mar. 19, 2009

(65) Prior Publication Data
US 2010/0330564 A1    Dec. 30, 2010

(30) Foreign Application Priority Data

Sep. 11, 2007 (JP) ................................ 2007-235935

(51) Int. Cl.
G01N 33/53    (2006.01)
C12Q 1/68     (2006.01)
G01N 33/566   (2006.01)

(52) U.S. Cl.
CPC .......... *G01N 33/5308* (2013.01); *C12Q 1/6844* (2013.01); *G01N 33/566* (2013.01)

(58) Field of Classification Search
None
See application file for complete search history.

(56) References Cited

U.S. PATENT DOCUMENTS

| 5,073,483 | A |   | 12/1991 | Lebacq |
| 5,482,836 | A | * | 1/1996  | Cantor et al. ................ 435/6.16 |
| 5,547,861 | A |   | 8/1996  | Nadeau et al. |
| 5,800,989 | A |   | 9/1998  | Linn et al. |
| 6,037,127 | A |   | 3/2000  | Ebersole et al. |
| 6,218,105 | B1 | * | 4/2001 | Hall et al. ........................ 435/5 |
| 2001/0036634 | A1 |   | 11/2001 | Chow et al. |
| 2003/0082559 | A1 |   | 5/2003  | Beach et al. |

(Continued)

FOREIGN PATENT DOCUMENTS

EP   0357011 A2   3/1990
JP   61-066964    4/1986

(Continued)

OTHER PUBLICATIONS

Horng et al. Development of an improved PCR-ICT hybrid assay for direct detection of *Legionellae* and *Legionella pneumophila* from cooling tower water specimens. Water Research 40:2221-2229 (2006).*

(Continued)

*Primary Examiner* — Samuel Woolwine
(74) *Attorney, Agent, or Firm* — Nixon & Vanderhye, PC

(57) ABSTRACT

In the present invention, an amplified DNA fragment having a first substance binding site to which a first substance is specifically bindable is prepared, which amplified DNA fragment amplified by a nucleic acid amplification method. The amplified DNA fragment is concentrated by binding the amplified DNA fragment to the first substance. The concentration makes it possible to detect the DNA highly sensitively. Therefore, with the arrangement, it is possible to detect the amplified DNA fragment amplified by the nucleic acid amplification method, easily and highly accurately without requiring any special device.

2 Claims, 4 Drawing Sheets

(56) References Cited

U.S. PATENT DOCUMENTS

| | | | |
|---|---|---|---|
| 2003/0129632 A1 | 7/2003 | Mori et al. | |
| 2003/0162237 A1* | 8/2003 | Griffiths | 435/7.92 |
| 2005/0227275 A1 | 10/2005 | Jung et al. | |
| 2006/0127907 A1 | 6/2006 | Matsubara et al. | |
| 2008/0003568 A1 | 1/2008 | Schmidt et al. | |
| 2008/0318238 A1 | 12/2008 | Matsubara et al. | |
| 2009/0142757 A1* | 6/2009 | Chou et al. | 435/6 |
| 2010/0120033 A1* | 5/2010 | Tomigahara et al. | 435/6 |
| 2010/0136531 A1* | 6/2010 | Garthwaite et al. | 435/6 |

FOREIGN PATENT DOCUMENTS

| | | |
|---|---|---|
| JP | 2002-186481 | 7/2002 |
| JP | 2003-000299 | 1/2003 |
| WO | 90/06374 A1 | 6/1990 |
| WO | WO 9006374 A1 * | 6/1990 |
| WO | 01/30993 | 5/2001 |
| WO | 02/04670 A2 | 1/2002 |
| WO | 2004/042084 A1 | 5/2004 |
| WO | 2004/099438 A1 | 11/2004 |
| WO | WO 2005/085440 A1 | 9/2005 |

OTHER PUBLICATIONS

English translation of the International preliminary report on patentability (Chapter I) of PCT Application No. PCT/JP2008/065307.

European Search Report for European Patent Application No. 08831240.0, mailing date of Jan. 4, 2011.

Glynou K. et al: "Oligonucleotide-Funcitionalized Gold Nanoparticles as Probes in a Dry-Reagent Strip Biosensor for DNA Analysis by Hybridization" Analytical Chemistry, American Chemical Society, US, vol. 75, No. 16, Aug. 15, 2003 pp. 4155-4160.

Reinhartz A. et al: "A Novel rapid hybridization technique: paper chromatography hybridization assay (PACHA)" Gene Elsevier, Amsterdam, NL vol. 136, No. 1-2, Dec. 22, 1993, pp. 221-226.

Baeumer Antje J. et al: "A universal nucleic acid sequence biosensor with nanomolar detection limits" Analytical Chemistry Feb. 15, 2004 LNKD-PUBMED:1496 vol. 76, No. 4, Feb. 15, 2004, pp. 888-894.

International Search Report for PCT/JP2008/065307, mailed Oct. 14 2008.

Hiratsuka et al., "Genotyping of Single Nucleotide Polymorphisms (SNPs) Influencing Drug Response by Competitive Allele-Specific Short Oligonucleotide Hybredization (CASSOH) with Immunochromatographic Strip", Drug Metabolism & Pharmacokinetics, vol. 19, No. 4, 2004, pp. 303-307.

Shiraishi et al., "Methyl-CpG Binding Domain Column Chromatography as a Tool for the Analysis of Genomic DNA Methylation", Analytical Biochemistry, 2004, vol. 329, No. 1, pp. 1-10.

Himanshu Gadgil et al., "Affinity Purification of DNA-Binding Proteins", Journal of biochemical and biophysical methods, 2001, vol. 49, No. 1-3, pp. 607-624.

Himanshu Gadgil et al., "DNA Affinity Chromatography of Transcription Factors", Analytical Biochemistry, 2001, vol. 290, No. 2, pp. 147-178.

Potuzak et al., "Affinity Chromatography on Columns Containing Nucleic Acids", FEBS letters, 1978, vol. 88 No. 2, pp. 161-166.

Wahlberg J et al: "General Colorimetric Method for DNA Diagnostics Allowing Direct Solid-Phase Genomic Sequencing of the Positive Samples", Proceedings of the National Academy of Sciences of USA, vol. 87 No. 17, Sep. 1, 1990, pp. 6569-6573,XP000268594,ISSN:0027-8424,DOI:10.1073/PNAS.87.17.6569 Sep. 1, 1990.

Lau P P et al:"A rapid method for the purification of supercoiled PM2 DNA by Affinity chromatography on H1 histone covalently coupled to agarose."Biochimica Et Biophysica Acta, vol. 563, No. 2, Jul. 26, 1979,pp. 313-319,XP024781976,ISSN:0005.2787, DOI:10.1016/0005-2787(79)90050-9[retrieved on Jul. 26, 1979] 07126 / 1979.

King M et al:"Immunoaffinity concentration of human lung DNA adducts using an anti-benzo [a]pyrene-diol epoxide-DNA antibody. Analysis by 32P-postlabelling or ELISA", Mutation Research/Environmental Mutagenesis and Related Subjects,vol. 292 No. 2, Oct. 1, 1993, pp. II3-122, XP025222140,ISSN:0165-1161,DOI:10.1016/0165-1161(93)90138-P[retrieved on Oct. 1, 1993].

Ge Hui:"UPA, a universal protein array system for quantitative detection of protein-protein, protein-DNA, protein-RNA and protein-ligand interactions." Nucleic Acids Research,vol. 28, No. 2, Jan. 15, 2000,pp. I-8, XP002355539,ISSN:0305-1048,DOI:10.1093/NAR/28.2.E3 Jan. 15, 2000.

Bowen B et al: "The detection of DNA-binding proteins by protein blotting." Nucleic Acids Research Jan. 11, 1980 LNKD-PUBMED:6243775, vol. 8, No. 1, Jan. 11, 1980, pp. I-20,ISSN:0305-1048 Jan. 11, 1980.

* cited by examiner

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:Synthesized
      Oligonucleotide

<400> SEQUENCE: 1
gctcgaattc actggccgtc g                                          21

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:Synthesized
      Oligonucleotide

<400> SEQUENCE: 2
ctatggatcc tacgccagct ggcgaaaggg                                 30
```

NUCLEIC ACID DETECTION METHOD AND NUCLEIC ACID DETECTION KIT

This application is the U.S. national phase of International Application No. PCT/JP2008/065307, filed 27 Aug. 2008, which designated the U.S. and claims priority to Japanese Patent Application No. 2007-235935, filed 11 Sep. 2007 the entire contents of each of which are hereby incorporated by reference.

TECHNICAL FIELD

The present invention relates to a nucleic acid detection method and a nucleic acid detection kit, more specifically, a nucleic acid detection method and a nucleic acid detection kit, each of which detects a nucleic acid amplified by a nucleic acid amplification method.

BACKGROUND ART

There have been known various nucleic acid amplification methods, such as an LAMP (Loop-Mediated Isothermal Amplification) method, an ICAN (Isothermal and Chimeric primer-initiated Amplification of Nucleic acids) method, and a PCR (Polymerase Chain Reaction; hereinafter, referred to as "PCR" in some cases) method. Among these, the PCR method has been widely used to amplify a nucleic acid, in the molecular biology field. In recent years, the PCR has been used more widely, so that it is applied not only to the molecular biology field but also to detection of a pathogen, detection of a substance (such as an allergen) mixed in a food product, livestock management, detection of a single nucleotide polymorphism (hereinafter, referred to "SNP" in some cases), etc.

Any usage of the PCR requires detection of a nucleic acid fragment amplified by the PCR. A great number of methods have been already known as a method for detecting an amplified nucleic acid fragment amplified by the PCR.

A most typical method for detecting the amplified nucleic acid fragment is such that (i) a solution which has been subjected to an amplification reaction is applied to agarose gel electrophoresis, and treated with a fluorescent intercalator, such as an ethidium bromide, for binding to the amplified nucleic acid fragment, and (ii) thereby the amplified nucleic acid fragment is observed for specific fluorescence.

Other than this method, for example, Patent Literature 1 discloses a method in which a nucleic acid amplification reaction is carried out with the use of a fluorescently-labeled primer, so that an amplified nucleic acid product is detected by means of fluorescence polarization. Further, Patent Literature 2 discloses a method for detecting an amplified nucleic acid fragment by (i) passing polarized light through a reaction solution subjected to the nucleic acid amplification reaction, and (ii) measuring an angle of rotation or a circular dichroism of the polarized light.

Furthermore, Patent Literature 3 discloses a method for detecting whether or not the nucleic acid amplification occurs, by (i) amplifying a target region on a polynucleotide chain, and (ii) detecting precipitating magnesium pyrophosphate while the amplification reaction proceeds. Moreover, Patent Literature 4 discloses a method in which (i) pyrophoric acid, produced in a polymerase extension reaction based on a specific base sequence of a target nucleic acid fragment, is treated with an enzymatic reaction reagent containing an oxidase, (ii) electron transfer that occurs during the action of the oxidase is amplified under the presence of an electrochemically active intercalator, and (iii) the amplified electron transfer is electrochemically detected as a current.

The techniques disclosed in Patent Literatures 1 through 4 allow the detection of the amplified nucleic acid fragment amplified by the nucleic acid amplification reaction. For the detection of the amplified nucleic acid fragment amplified by the PCR, any nucleic acid detection method is applicable.

As the nucleic acid detection method, for example, Patent Literature 5 discloses a method for detecting a nucleic acid by enzymatically coloring a nucleic acid sequence immobilized to a solid support.

Further, Patent Literature 6 discloses a method for detecting a nucleic acid by dyeing the nucleic acid with a metal and reacting the metal-dyed nucleic acid with a dye precursor and an auxiliary agent.

CITATION LIST

Patent Literature 1
Japanese Patent Application Publication, Tokukaihei, No. 09-187275 A (1997)(Publication Date: Jul. 22, 1997)
Patent Literature 2
Japanese Patent Application Publication, Tokukai, No. 2002-186481 A (Publication Date: Jul. 2, 2002)
Patent Literature 3
International Publication No. WO 01/83817 (Publication Date: Nov. 8, 2001)
Patent Literature 4
Japanese Patent Application Publication, Tokukai, No. 2003-299 A (Publication Date: Jan. 7, 2003)
Patent Literature 5
Japanese Patent Application Publication, Tokukaihei, No. 02-9400 A (Publication Date: Jan. 12, 1990)
Patent Literature 6
Japanese Patent Application Publication, Tokukaisho, No. 61-66964 A (Publication Date: Apr. 5, 1986)

SUMMARY OF INVENTION

As described above, there are various methods for detecting the nucleic acid amplified fragment amplified by the PCR, but in view of simplicity, speediness, accuracy, etc., any of these methods has a problem.

For example, with the method of dying the amplified nucleic acid fragment with the ethidium bromide after the electrophoresis, the electrophoresis takes time, and a device or equipment for detecting the fluorescence are necessary. If a nucleic acid other than the target amplified nucleic acid fragment amplified by the PCR is quantitatively ignorable, it would be possible to omit the electrophoresis step. However, even in this case, the device or equipment for detecting the fluorescence is necessary.

The method disclosed in Patent Literature 1 has such a problem that it requires an additional step of separating a free fluorescently-labeled primer left unbonded to the amplified nucleic acid fragment in the nucleic acid amplification reaction. Further, the operation to separate the primer may decrease a yield of the amplified nucleic acid fragment obtained by the PCR. As a result, this method may decrease a detection sensitivity.

Furthermore, the detection by significantly simple precipitation makes the method disclosed in Patent Literature 3 seem to be practical, but the method has a problem of a low detection sensitivity. Moreover, the method disclosed in Patent Literature 4 has a problem in simplicity due to its complicated operation.

In the similar manner, the methods disclosed in Patent Literatures 5 and 6 also have a problem that their processes are complicated.

As described above, not only the methods for detecting the amplified DNA fragment amplified by the PCR method but also each method for detecting the amplified DNA fragment amplified by a conventional nucleic acid amplification method has a problem, and development of a novel technique is further demanded.

The present invention is made in view of the problems. An object of the present invention is to provide a nucleic acid detection method and a nucleic acid detection kit, each of which makes it possible to detect an amplified DNA fragment amplified by a nucleic acid amplification method, easily and highly accurately without requiring any special device.

As a result of diligent study in view of the problems described above, the inventors of the present invention uniquely found that, by designing a primer so that a specific substance can specifically bind to both end regions of an amplified DNA fragment obtained from nucleic acid amplification of a gene sample, it becomes possible to detect, by use of the specific substance, the amplified DNA fragment easily and highly accurately without requiring any specific device. Based on the finding, the inventors of the present invention accomplished the present invention. That is, the scope of the present invention encompasses the following industrially-useful inventions:

(1) A nucleic acid detection method for detecting an amplified double-stranded DNA fragment amplified by a nucleic acid amplification method, wherein: the amplified DNA fragment has a first substance binding site to which a first substance is specifically bindable; and the nucleic acid detection method includes the step of: concentrating the amplified DNA fragment by causing the amplified DNA fragment to bind to the first substance.

(2) The nucleic acid detection method as set forth in (1), wherein: the amplified DNA fragment is a double-stranded DNA fragment obtained by the nucleic acid amplification method by use of two primers; and at least one of the two primers has a base sequence to which the first substance is bindable in a double strand formed by binding the at least one of the two primers to a complementary strand.

(3) The nucleic acid detection method as set forth in (1) or (2), wherein: said step of concentrating including: (i) placing the amplified DNA fragment on a stationary-phase medium to which the first substance is immobilized, the amplified DNA fragment being placed in a first region of the stationary-phase medium different from a second region of stationary-phase medium in which the first substance is immobilized, (ii) diffusing the amplified DNA fragment by use of a solvent on the stationary-phase medium to the second region; and (iii) binding the amplified DNA fragment to the first substance in the second region.

(4) The nucleic acid detection method as set forth in (1), wherein: the amplified DNA fragment further has a second substance binding site to which a second substance is specifically bindable; and said step of concentrating including: (i) forming a complex by binding the amplified DNA fragment to the second substance to which a labeling substance is bound, and (ii) binding the complex to the first substance.

(5) The nucleic acid detection method as set forth in (4), wherein: the amplified DNA fragment is a double-stranded DNA fragment obtained by the nucleic acid amplification method by use of two primers; one of the two primers has a base sequence to which the first substance is bindable in a double strand formed by binding the one of the two primers to a complementary strand; and the other one of the two primers has a base sequence to which the second substance is bindable in a double strand formed by binding the other one of the two primers to a complementary strand.

(6) The nucleic acid detection method as set forth in (4) or (5), wherein: said step of concentrating including: (i) on a stationary-phase medium to which the first substance is immobilized, placing the amplified DNA fragment in a first region, and placing the second substance to which the labeling substance is bound in a third region, the first region and third region being different from each other and being different from a second region in which the first substance is immobilized, (ii) diffusing the amplified DNA fragment by use of a solvent to the third region, (iii) forming a complex in the third region by binding the amplified DNA fragment to the second substance to which the labeling substance is bound, (iv) diffusing the complex on the stationary-phase medium to the second region by use of the solvent, and (v) binding the first substance and the complex to each other in the second region.

(7) The nucleic acid detection method as set forth in any one of (4) through (6), wherein: the first substance and the second substance are different from each other.

(8) The nucleic acid detection method as set forth in any one of (1) through (7), wherein: the first substance is a nucleic acid binding protein.

(9) The nucleic acid detection method as set forth in any one of (4) through (6), wherein: the second substance is a nucleic acid binding protein.

(10) A stationary-phase medium for detecting an amplified double-stranded DNA fragment amplified by a nucleic acid amplification method, including: a first region for placing the amplified DNA fragment therein; and a second region in which a first substance specifically bindable to the amplified DNA fragment is able to be immobilized.

(11) The stationary-phase medium as set forth in (10), further including: a third region for placing a second substance to which a labeling substance is bound, the second substance being specifically bindable to the amplified DNA fragment.

(12) The stationary-phase medium as set forth in (11), still further including: a fourth region in which a nucleic acid fragment specifically bindable to the second substance is able to be immobilized.

(13) The stationary-phase medium as set forth in any one of (10) through (12), wherein: the first substance is immobilized in the second region.

(14) The stationary-phase medium as set forth in (12), wherein: the nucleic acid fragment specifically bindable to the second substance is immobilized in the fourth region.

(15) The stationary-phase medium as set forth in any one of (10) through (14), wherein: the first substance is a nucleic acid binding protein.

(16) The stationary-phase medium as set forth in (11) or (12), wherein: the second substance is a nucleic acid binding protein.

(17) A nucleic acid detection kit for detecting an amplified double-stranded DNA fragment amplified by a nucleic acid amplification method, the nucleic acid detection kit including: a stationary-phase medium as set forth in any one of (10) through (16).

(18) The nucleic acid detection kit as set forth in (17), further including: a first primer having a base sequence to which a first substance is bindable in a double strand formed by binding the first primer to a complementary strand.

(19) The nucleic acid detection kit as set forth in (18), still further including: a second primer having a base sequence to which a second substance is bindable in a double strand formed by binding the second primer to a complementary strand.

(20) The nucleic acid detection kit as set forth in (19), yet still further including: the second substance to which a labeling substance is bound.

Additional objects, features, and strengths of the present invention will be made clear by the description below. Further, the advantages of the present invention will be evident from the following explanation in reference to the drawings.

DESCRIPTION OF EMBODIMENTS

Figure 1:
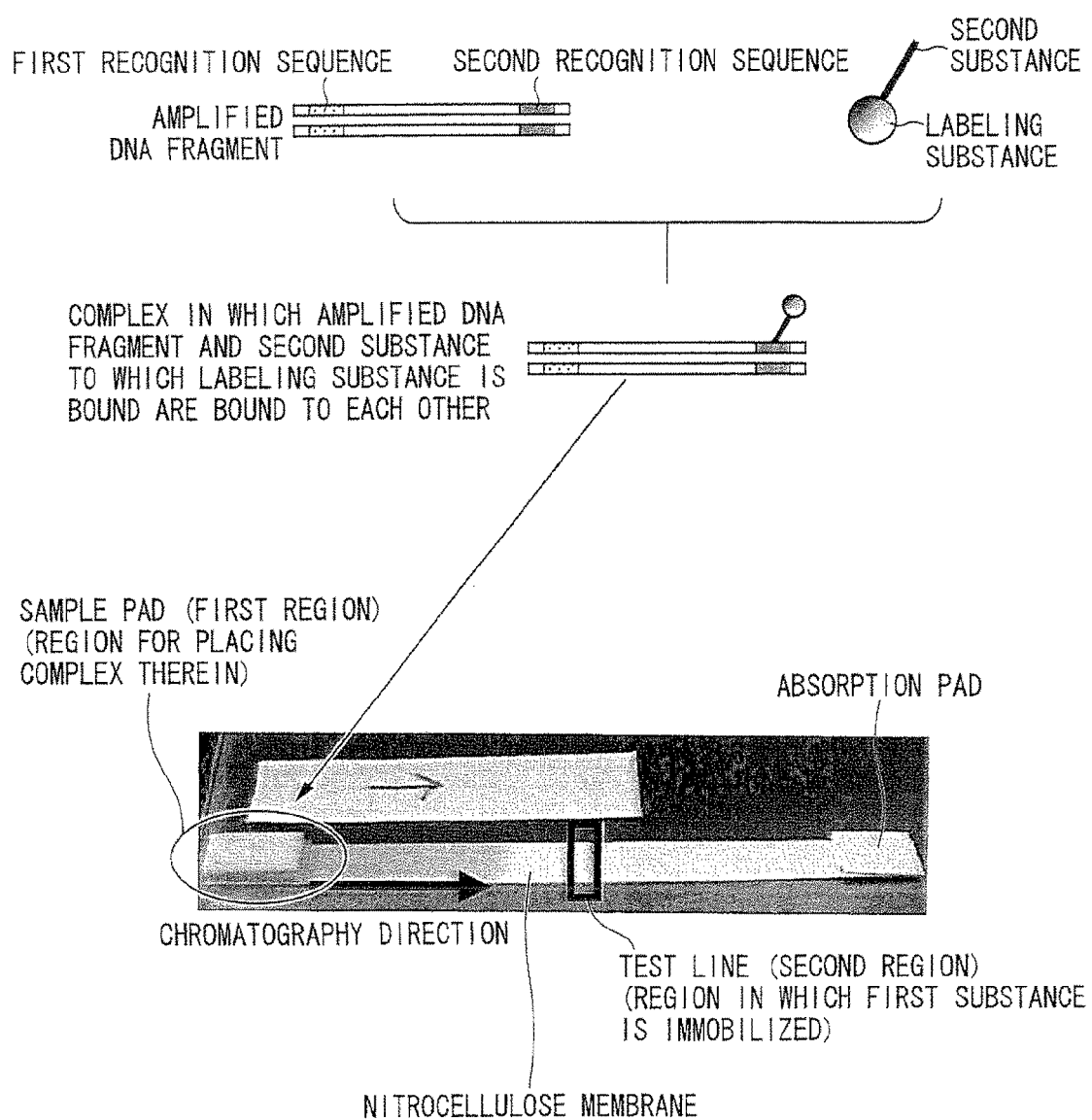
FIG. 1 is a view schematically showing a principle of a nucleic acid detection method in accordance with an embodiment of the present invention.

One embodiment of the present invention is described below with reference to FIGS. 1 through 4. It should be noted that the present invention is not limited to the embodiment.
<I. Nucleic Acid Detection Method>

A nucleic acid detection method of the present invention only has to include at least a step of concentrating an amplified DNA fragment by binding, to a first substance an amplified double-stranded DNA fragment amplified by a nucleic acid amplification method, the first substance being specifically bindable to the amplified double-stranded DNA fragment (hereinafter, referred to as "amplified DNA fragment concentration step" in some cases).

With the arrangement, the amplified DNA fragment can specifically bind to the first substance. Accordingly, by taking advantage of affinity between the amplified DNA fragment and the first substance, it is possible to concentrate the amplified DNA fragment. Specifically, for example, the first substance is immobilized to a carrier or the like, so that it is possible to easily concentrate the amplified DNA fragment by use of the aforementioned carrier to which the first substance is immobilized.

By concentrating the amplified DNA fragment as described above, it becomes possible to detect the amplified DNA fragment based on a principle totally different from those of conventionally-known methods. Note that in the specification of the present invention, "nucleic acid amplification method" is any method for amplifying a nucleic acid. More specifically, the nucleic acid amplification method may be a PCR method, an LAMP method, an ICAN method, etc.

Further, "detecting an amplified DNA fragment" may be not only direct detection of the amplified DNA fragment but also indirect detection of the amplified DNA fragment by detecting a substance binding to the amplified DNA fragment.

As another embodiment, the nucleic acid detection method of the present invention can have an arrangement including the steps of: forming a complex by binding, to a second substance to which a labeling substance is bound, an amplified double-stranded DNA fragment amplified by a nucleic acid amplification method, the second substance being specifically bindable to the amplified DNA fragment (hereinafter, this step is referred to as "complex forming step" in some cases); and concentrating the amplified DNA fragment (i.e. the complex) by binding the complex to the first substance which can specifically bind to the amplified DNA fragment (hereinafter, this step is referred to as "amplified DNA fragment concentration step" in some cases).

This arrangement allows the amplified DNA fragment to specifically bind to both the first and second substances. In the arrangement, first, the amplified DNA fragment is caused to bind to the second substance to which the labeling substance is bound. This forms the complex in which the amplified DNA fragment and the second substance to which the labeling substance is bound, are bound to each other.

Since the complex contains the amplified DNA fragment, it can specifically bind to the first substance. Therefore, by taking advantage of the affinity between the complex and the first substance, the complex can be concentrated. It follows that the amplified DNA fragment can be concentrated. Here, the labeling substance is also concentrated in the similar manner while the amplified DNA fragment is concentrated.

Therefore, with the arrangement, it is possible to indirectly detect the amplified DNA fragment by detecting the labeling substance thus concentrated.

As described above, according to the nucleic acid detection method of the present invention, it becomes possible to efficiently concentrate the amplified DNA fragment by use of a substance having an affinity with the amplified DNA fragment. Therefore, it is possible to detect the amplified DNA fragment easily and highly accurately (highly sensitively) without requiring any special device.

In any of the embodiments described above, the nucleic acid detection method of the present invention may further include the step of obtaining the amplified DNA fragment by nucleic acid amplification of a DNA sample (hereinafter, referred to as "nucleic acid amplification step" in some cases).

The following description mainly deals with, as one embodiment of the nucleic acid detection method of the present invention, an embodiment in which an amplified DNA fragment amplified by the PCR method is detected. It should be noted that the present invention is not limited to the embodiment. That is, a person skilled in the art can easily understand that any nucleic acid amplification method is applicable with a template and a primer designed for the nucleic acid amplification method, in order to use the nucleic acid detection method of the present invention to detect the amplified double-stranded DNA fragment amplified by the nucleic acid amplification method.

As described above, the description here discusses one non-limiting exemplary embodiment of the nucleic acid detection method of the present invention, including the PCR step (nucleic acid amplification step), the complex forming step, and the DNA fragment concentration step, thereby describing these steps more specifically. It should be noted that the present invention is not limited to this embodiment.
(I-1) PCR Step In the PCR step, the PCR is carried out by use of a certain primer set with respect to a DNA sample serving as a template. The PCR provides an amplified DNA fragment. The following description deals with: the DNA sample used in the PCR step; the primer used in the PCR step; and PCR conditions, more specifically.
[DNA Sample]

The DNA sample serving as the template is not particularly limited as long as it is DNA that can serve as the template for the PCR. Specifically, the DNA sample may be DNA derived from any of biological samples of animals, plants, microorganisms, etc. For example, blood, a body fluid, a tissue, an interoral mucous membrane, a hair, a nail, or a cultured cell may be used as the biological sample. Further, the DNA sample may be any one of genomic DNA, cDNA, mitochondrial DNA, and chloroplast DNA (plastid DNA), for example. The DNA sample may be selected from these appropriately in accordance with the DNA fragment to be amplified.

Further, in the PCR step, the DNA fragment to be amplified (i.e. the amplified. DNA fragment) is not particularly limited, as long as it has a partial base sequence of the DNA sample serving as the template. Specifically, the DNA fragment may be a translated region, a untranslated region, a partial region of the translated region, or a partial region of the untranslated region, for example. Further, a length of the amplified DNA fragment is also not particularly limited, but it is preferable that the length is in a range of 50 bp to 1000 bp.

Note that as to the DNA sample, it is preferable that the base sequence of the region to be amplified by the PCR has been already known. However, even if it is unknown, it would only have to find out and define such a base sequence. Further, it is preferable to select the region to be amplified by the PCR in consideration of the design of the primer. However, there have been known a great number of means for overcoming problems in designing the primer, and a person skilled in the art ordinarily designs the primer by appropriate combinations of such means. That is, needless to explain here, determining the region to be amplified by the PCR, or designing the primer can be easily performed by adopting appropriate combination of the means ordinarily used by a person skilled in the art.

Further, the amplified DNA fragment has a first substance binding site to which the first substance can specifically bind. That is, the amplified DNA fragment has a base sequence being the first substance binding site. It is preferable that the first substance binding site is located in one of primer binding regions (regions derived from primer sequences) which are located at both ends of the amplified DNA fragment, respectively.

Further, it is preferable that the amplified DNA fragment further has a second substance binding site which can specifically bind to the second substance. That is, it is preferable that the amplified DNA fragment further has a base sequence being the second substance binding site. It is preferable that the second substance binding site is located in one of the primer binding regions (regions derived from the primer sequences) which are located at both ends of the amplified DNA fragment, respectively.

Each of the base sequence being the first substance binding site and the base sequence being the second substance binding site can be easily introduced into the amplified DNA fragment by performing the PCR with a primer whose base sequence has the above base sequence.

Other than the base sequence being the first substance binding site and the base sequence being the second substance binding site, the amplified DNA fragment may further have a base sequence which is not derived from the DNA sample. The base sequence not derived from the DNA sample may be a restriction enzyme recognition sequence, for example. Such a base sequence can be also added to the amplified DNA fragment by performing the PCR with a primer having the base sequence. Such a method has been conventionally-known by a person skilled in the art.

Note that the first substance, the second substance, and the base sequences to which the first substance and second substance specifically bind, respectively, will be described later, so that the detailed explanations of these are omitted here.

[Primer]

A primer set used in the PCR step is constituted by two primers which can amplify a desired region of the DNA sample.

At least one of the two primers has the base sequence to which the first substance is bindable in a double strand formed by binding the primer to a complementary strand. That is, the primer has the base sequence (hereinafter, this sequence is referred to as "first recognition sequence" in some cases) that gives a specific binding ability with respect to the first substance, to the amplified DNA fragment obtained by carrying out the PCR by using the DNA sample as the template.

Further, it is preferable that at least one of the two primers has the base sequence to which the second substance is bindable in a double strand formed by binding the primer to a complementary strand. That is, it is preferable that the primer has the base sequence (hereinafter, this sequence is referred to as "second recognition sequence") that gives a specific binding ability with respect to the second substance, to the amplified DNA fragment.

Note that in an embodiment which does not include the complex forming step, the nucleic acid detection method of the present invention may be such that the two primers do not include the second recognition sequence. In such an embodiment, it is preferable that at least one of the two primers is labeled with a labeling substance. More specifically, it is preferable that the at least one of the two primers is labeled with a radioactive isotope, or the like, for example.

Figure 2:
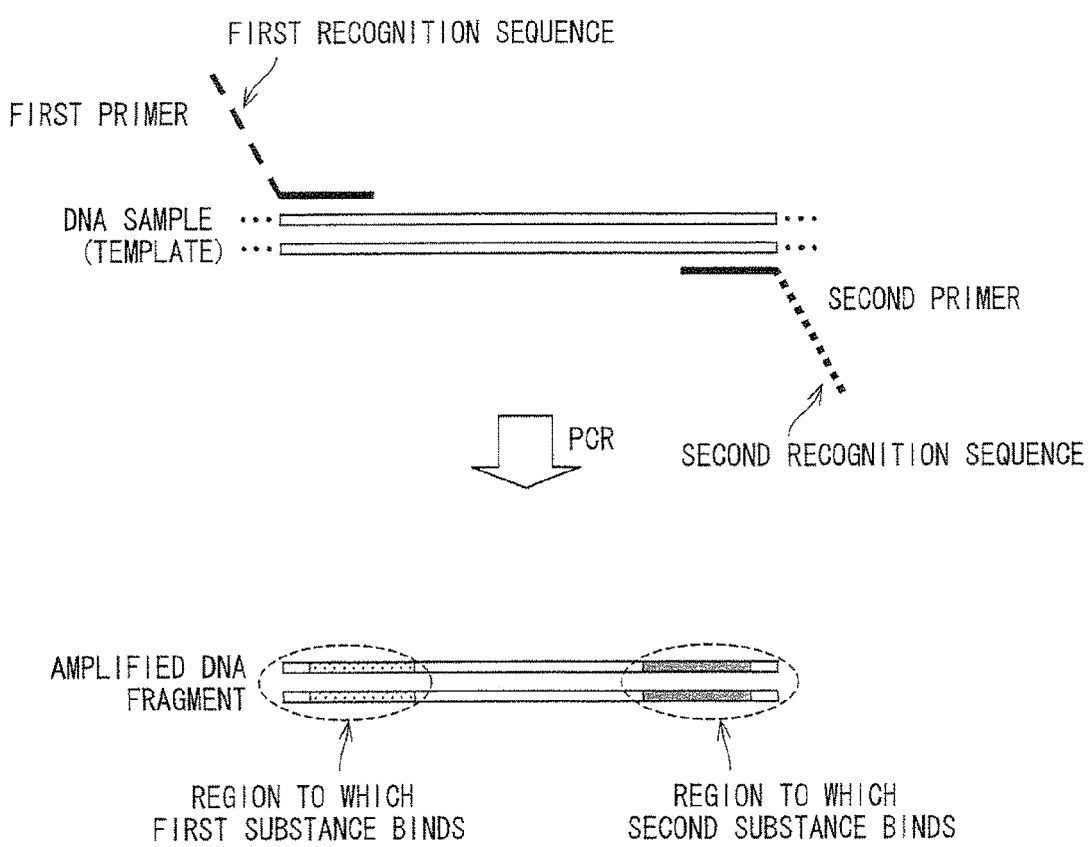
FIG. 2 is a view schematically showing a PCR step of the nucleic acid detection method in accordance with the embodiment of the present invention.

In a case where the two primers have the first recognition sequence and/or the second recognition sequence, the present invention can be embodied as any one of the following embodiments: (a) an embodiment in which one of the two primers has the first and second recognition sequences, and the other one of the two primers has none of them, (b) an embodiment in which, each of the two primers has the first and second recognition sequences, (c) an embodiment in which one of the two primers has the first and second recognition sequences, and the other one of the two primers has only the first recognition sequence, (d) an embodiment in which one of the two primers has the first and second recognition sequences, and the other one of the two primers has only the second recognition sequence, and (e) an embodiment in which one of the two primers has only the first recognition sequence, and the other one of the two primers has only the second recognition sequence. In the present invention, (e) the embodiment in which one of the two primers has only the first recognition sequence, and the other one of the two primers has only the second recognition sequence, is particularly preferable. If the PCR is carried out by using the primer set of (e) described above, it becomes possible to obtain such an amplified DNA fragment that one end (more specifically, a sequence region of the primer having the first recognition sequence) has the base sequence to which the first substance is bindable, and the other end (more specifically, a sequence region of the primer having the second recognition sequence) has the base sequence to which the second substance is bindable, as shown in FIG. 2.

The following description deals with (e) the embodiment in which one of the two primers has only the first recognition sequence, and the other one of the two primers has only the second recognition sequence. It should be noted that the present invention is not limited to this embodiment. A person skilled in the art can easily design the primer sets of the embodiments (a) through (d) according to the following description.

Further, in the specification of the present invention, in some cases, the primer having the first recognition sequence is referred to as "first primer", and the primer having the second recognition sequence is referred to as "second primer" for the sake of simple explanation.

The first and second substances only have to be the ones which can specifically recognize and bind to specific base sequences in the binding regions of the two primers, respectively, which binding regions are located at both ends of the amplified DNA fragment, respectively. Further, it is preferable that the first and second substances specifically recognize the double-stranded DNA.

If the first and second substances specifically recognize the double-stranded DNA, they can bind to the amplified DNA fragment amplified by the PCR, but cannot bind to any unreacted primer.

Therefore, even if the complex forming step or the amplified DNA fragment concentration step (which will be described later) is performed with a PCR reaction solution as such serving as a sample having the amplified DNA fragment, it is possible to detect the amplified DNA fragment free from an influence of the unreacted primer.

Each of the first and second substances is not particularly limited, and may be a protein having a region which can specifically bind to the base sequence. Particularly, it is preferable to use a protein which can specifically and strongly bind to a specific base sequence of a nucleic acid. More specifically, it is preferable to use a nucleic acid binding protein, or the like, for example.

Specifically, the nucleic acid binding protein may be, but not particularly limited to, a restriction enzyme, a methylase corresponding to the restriction enzyme, a transcription/translation factor, or a protein related to DNA modification, for example.

Examples of the restriction enzyme encompass AccI, AluI, ApaI, BamHI, BglII, BssHII, BstEII, ClaI, DdeI, DraI, EcoRI, EcoRV, HaeIII, HincII, HindIII, HpaI, HpaII, KpnI, MluI, NarI, NcoI, NdeI, NheI, NotI, PstI, PvuI, PvuII, RsaI, SacI, SalI, ScaI, SmaI, SpeI, SphI, Sspl, StuI, XbaI, and XhoI, for example.

Examples of the transcription/translation factor encompass a TATA box-binding protein, and a transcription factor such as Jun, Fos, ATF3, Maf, Nrf2, and Bach2.

The protein related to the DNA modification may be Dnmt, MAPK, or the like.

Note that the first and second substances may be either identical with each other or different from each other. In the present invention, however, it is preferable that these are different from each other.

Further, the first and second recognition sequences are not particularly limited as long as they are sequences which can be recognized site-specifically by the first and second substances, respectively. Furthermore, lengths of the respective first and second recognition sequences are not particularly limited as long as the first and second substances can recognize the first and second recognition sequences, respectively. Generally, it is preferable that each of the lengths is in a range of 2 bases to 20 bases, more preferably in a range of 4 bases to 12 bases.

Each of the first and second recognition sequences may be a recognition sequence of the restriction enzyme, a recognition sequence of the methylase corresponding to the restriction enzyme, a recognition sequence of the transcription/translation factor, or a recognition sequence of the protein related to the DNA modification, for example.

As to the restriction enzyme, the methylase corresponding to the restriction enzyme, the transcription/translation factor, and the protein related to the DNA modification, see the aforementioned description.

Further, the first and second recognition sequences may be either identical with each other, or different from each other. In the present invention, it is preferable that the first and second recognition sequences are different from each other.

Each of the two primers constituting the primer set has a base sequence hybridizable with the DNA sample (hereinafter, this sequence is referred to as "template binding sequence" in some cases), and at least one of the first and second recognition sequences. It is preferable that the template binding sequence is located closer to a 3' end than the first and/or second recognition sequences in each of the two primers.

With the arrangement, it is possible to efficiently amplify a specific region of the DNA sample by the PCR.

Further, each of the two primers may have a base sequence other than the template binding sequence and the first and/or second recognition sequences. For example, it is possible to add about 1 base to 5 bases to a 5' end of each of the two primers.

Further, each of the two primers may have, between its 3' end and the first or second recognition sequence, a sequence hybridizable with the template binding sequence and/or the first or second recognition sequence. Such a sequence is not particularly limited as long as it is a sequence to which the first and second substances cannot bind.

Further, a length of the sequence is not particularly limited, but it is preferable that the length is 2 bases to 20 bases, more preferably 4 bases to 12 bases.

With the arrangement including such a sequence, the primers form the double strand from themselves. Therefore, with the arrangement, if there is no target DNA to be amplified, the primers form the double strand from themselves so that nonspecific amplification, and subsequent nonspecific nucleic acid detection can be suppressed.

The two primers only have to have the template binding sequence and the first and/or second recognition sequences, and their lengths are not particularly limited. That is, the lengths may be determined in consideration of a Tm value or the like. The template binding sequence only has to have a length sufficient to hybridize with a specific region of the DNA sample. The length of the template binding sequence is not particularly limited, but generally, it is in a range of 15 bases to 30 bases, more preferably in a range of 18 bases to 25 bases.

Further, each of the first and second recognition sequences only has to have a length sufficient for the first and second substances to recognize it. The length of each of the first and second recognition sequences is generally, but not particularly limited to, in a range of 2 bases to 20 bases, more preferably in a range of 4 bases to 12 bases.

Further, it is preferable to design each of the two primers so that the amplified DNA fragment amplified by the PCR has a length in a range of 50 bp to 500 bp. By designing the primers so that such a condition is satisfied, it becomes possible to ensure that the amplified DNA fragment is obtained by the PCR. Note that the present invention is, of course, not limited to this.

A method for producing the designed primers is not particularly limited, and may be a conventionally-known method. Specifically, the primers can be produced by use of a DNA synthesizer. Further, the designed primers are easily available from a oligo-oligonucleotide synthesis service (commercial service), which tailors the primers. Further, each of the primers thus produced may be purified by HPLC.

Note that the description here deals with the design of the primers used in the PCR method, however, in a case where the nucleic acid amplification is carried out by an isothermal nucleic acid amplification method, such as the LAMP method or the ICAN method, the primers may be also designed to have the first recognition sequence, and, if necessary, further have the second recognition sequence.

[PCR Condition]

The PCR condition in the PCR step is not particularly limited, as long as the condition allows the PCR to amplify the desired region of the DNA sample by use of the primer set and the DNA sample as the template.

Specifically, a DNA polymerase used in the PCR step is not particularly limited, but it is preferable that the DNA polymerase is a heat-stable DNA polymerase, more preferably a heat-stable polymerase that does not substantially have a 3'-to-5' exonuclease activity. Such a heat-stable DNA polymerase may be Platinum Taq (manufactured by GIBCO Co.), Ampli-Taq (manufactured by Applied Biosystems or Ex-Taq (manufactured by TaKaRa Co.), for example.

Further, reaction conditions of the PCR (specifically, a temperature, a time, a buffer solution composition, etc. in the PCR) is not particularly limited, and may be determined in accordance with the DNA polymerase selected to use, the sequence of the primer, the length of the target sequence part, etc.

As an example, if the DNA polymerase is Ex-Taq, the PCR can be carried out with the following temperature cycle repeated 25 to 35 times: (i) the PCR reaction solution is heated at a temperature of 94° C. for 30 seconds to 2 minutes; (ii) denaturing is carried out at the temperature of 94° C. for 30 seconds; (iii) annealing is carried out at a temperature in a range of 55° C. to 60° C. (which temperature is determined based on the Tm value found based on the primer sequence by a conventionally-known method) for 30 seconds; and (iv) elongation is performed at a temperature of 72° C. for 1 minute per 1 kb. After the PCR is finished, the PCR reaction solution can be stably preserved at a temperature of 4° C.

(I-2) Complex Forming Step

In the complex forming step, the amplified DNA fragment obtained in the PCR step is caused to bind to the second substance to which the labeling substance is bound. In this way, a complex is formed. Note that in the case of the embodiment in which the amplified DNA fragment does not have the ability to bind to the second substance, the complex forming step is unnecessary.

The second substance to which the labeling substance is bound is such that a labeling substance is bound to said second substance. The labeling substance is not particularly limited, and may be a labeling substance which can bind to the second substance, which labeling substance may be selected in accordance with the second substance.

Specifically, if the second substance is the nucleic acid binding protein, the labeling substance may be any conventionally-known substance for labeling a protein, for example. Examples of such a labeling substance encompass colored particles, an enzyme, and a fluorescent material.

Specific examples of the colored particles encompass: colloid particles made from a metal such as gold, silver, copper, or the like; and a colored latex which is a latex dyed with a pigment or dye, represented by Sudan Blue, Sudan Red IV, Sudan III, Oil Orange, Quinizarine Green, etc. Similarly, specific examples of the enzyme encompass: alkaline phosphatase; peroxidase; etc. Further, specific examples of the fluorescent material encompass: FITC; rhodamine; etc.

Among these, in the present invention, it is preferable to use the colored particles as the labeling substance. The colored particles are detectable with the naked eye. Accordingly, in the amplified DNA fragment concentration step, it is possible to detect the amplified DNA fragment visually after concentrating the amplified DNA fragment. Therefore, with the arrangement, it is possible to detect the amplified DNA fragment amplified by the PCR more easily, without requiring any special device.

Further, among the examples of the colored particles described above, it is preferable to use gold colloid, or the colored latex colored in blue, red, green, or orange. With such colored particles, it becomes possible to detect the amplified DNA fragment visually more easily.

Further, it is more preferable that the colored particles are a colored latex made from a water dispersion high molecular weight polymer colored in blue, red, or the like. With such a colored latex, the second substance to which the labeling substance is bound can be dispersed into an aqueous solvent stably, and the detection sensitivity of the amplified DNA fragment can be easily adjusted.

The colored particles used as the labeling substance are not particularly limited in terms of particle diameter. However, it is preferable that the colored particles have a particle diameter that does not significantly adversely affects the operation of the complex forming step and the amplified DNA fragment concentration step, while allowing excellent color development for the detection of the amplified DNA fragment. In consideration of this, the diameter of each of the colored particles is preferably in a range of 0.1 nm to 50 nm, more preferably in a range of 1 nm to 10 nm. If the diameter is in the range described above, the colored particles would be easy to prepare, and be in excellent in preservation stability.

More specifically, if the complex forming step and the amplified DNA fragment concentration step are carried out in such a manner that the amplified DNA fragment and the second substance to which the labeling substance is bound are diffused on the stationary-phase medium with the use of the aqueous solvent, the colored particles having a particle diameter greater than the range described above would cause clogging of a water absorbing substrate even by slight aggregation of the colored particles. Such clogging will result in that the water-absorbability is decreased or nonspecific color development is generated. That is, in such an embodiment, it is preferable that the colored particles have a particle diameter which realizes mobility in the water absorbing substrate to such a degree that the water absorbing substrate is not decreased in water-absorbability.

The method for binding the labeling substance to the second substance (in other words, the method for labeling the second substance with the labeling substance) is not particularly limited, and may be selected appropriately in accordance with the combination of the second substance and the labeling substance.

For example, if the second substance is the nucleic acid binding protein, and the labeling substance is the colored particles, it would be possible to bind the colored particles to the nucleic acid binding protein by a conventionally-known method such as a covalent bonding method, a physisorption method, an ion bonding method, or the like. Among these, it is preferable to use the covalent bonding method to cause the colored particles to bind to the nucleic acid protein. With such an arrangement, the colored particles and the nucleic acid binding protein bind to each other strongly, so that the colored particles would not separate from the second substance but maintain stable binding either in the complex forming step or in the amplified DNA fragment concentration step.

The complex forming step is not particularly limited as to how to form the complex by binding the amplified DNA fragment to the second substance to which the labeling substance is bound. The complex forming step may be carried out by any method as long as the method can cause the amplified DNA fragment and the second substance to bind to each other.

For example, the complex can be formed by mixing a solution containing the amplified DNA fragment and another solution containing the second substance to which the labeling substance is bound (including a dispersion liquid in which the second substance to which the labeling substance is bound is dispersed in a dispersion medium) together. Note that necessary catalysts or substances may be arbitrarily added to the mixed solution in accordance with a kind of the binding or a binding reaction between the amplified DNA fragment and the second substance.

Further, the medium for dissolving or dispersing the amplified DNA fragment and the second substance to which the labeling substance is bound is not particularly limited, and may be a medium suitable for the binding reaction between them. Specifically, it is preferable that the medium is a buffer solution having a pH and a salt level suitable for the binding reaction between them. With such a buffer solution, the binding reaction between them cannot be inhibited. The buffer solution is also not particularly limited, but is preferably a buffer solution usable to dissolve the nucleic acid therein. Specific examples of the buffer solution encompass: a phosphate buffer solution; an acetic acid buffer solution; a boric acid buffer solution; and a Tris-HCl buffer solution.

As another embodiment of the method for forming the complex, the complex can be formed in such a manner that (i) the solution containing the amplified DNA fragment and the solution containing the second substance to which the labeling substance is bound are respectively placed in separate regions on a stationary-phase medium including the water absorbing substrate, and (ii) the amplified. DNA fragment is diffused on the stationary-phase medium by use of the solvent, so as to form the complex in the region where the second substance to which the labeling substance is bound is present. Note that the second substance to which the labeling substance is bound may be diffused, so as to form the complex in the region where the amplified DNA fragment is present.

(I-3) DNA Fragment Concentration Step

In the DNA fragment concentration step, the complex formed in the complex forming step is caused to bind to the first substance, so as to be concentrated, that is, the amplified DNA fragment is concentrated.

Note that in the embodiment in which the amplified DNA fragment does not have the ability to bind to the second substance, the amplified DNA fragment is concentrated in such a manner that the amplified DNA fragment is caused to bind to the first substance in the DNA fragment concentration step.

The method for concentrating the amplified DNA fragment or the complex by causing the amplified DNA fragment or the complex to bind to the first substance is not particularly limited, and may be any method as long as the method takes advantage of the affinity (binding ability) between the amplified DNA fragment and the first substance.

Specifically, for example, the amplified DNA fragment or the complex can be concentrated in such a manner that (i) a carrier to which the first substance is immobilized, and the amplified DNA fragment or the complex are mixed together, so that the amplified DNA fragment or the complex binds to the first substance, and then (ii) the carrier is collected.

Further, as another embodiment (see FIG. 1), the amplified DNA fragment or the complex can be concentrated in such a manner that (i) the first substance is immobilized to a partial region (see TEST LINE in FIG. 1) of the stationary-phase medium, (ii) the amplified DNA fragment or the complex is placed on the stationary-phase medium in a region (see SAMPLE PAD in FIG. 1) different from the region where the first substance is immobilized on the stationary-phase medium, (iii) the amplified DNA fragment or the complex is diffused by use of the solvent, and (iv) the amplified DNA fragment or the complex is captured in the region where the first substance is immobilized.

Figure 3:
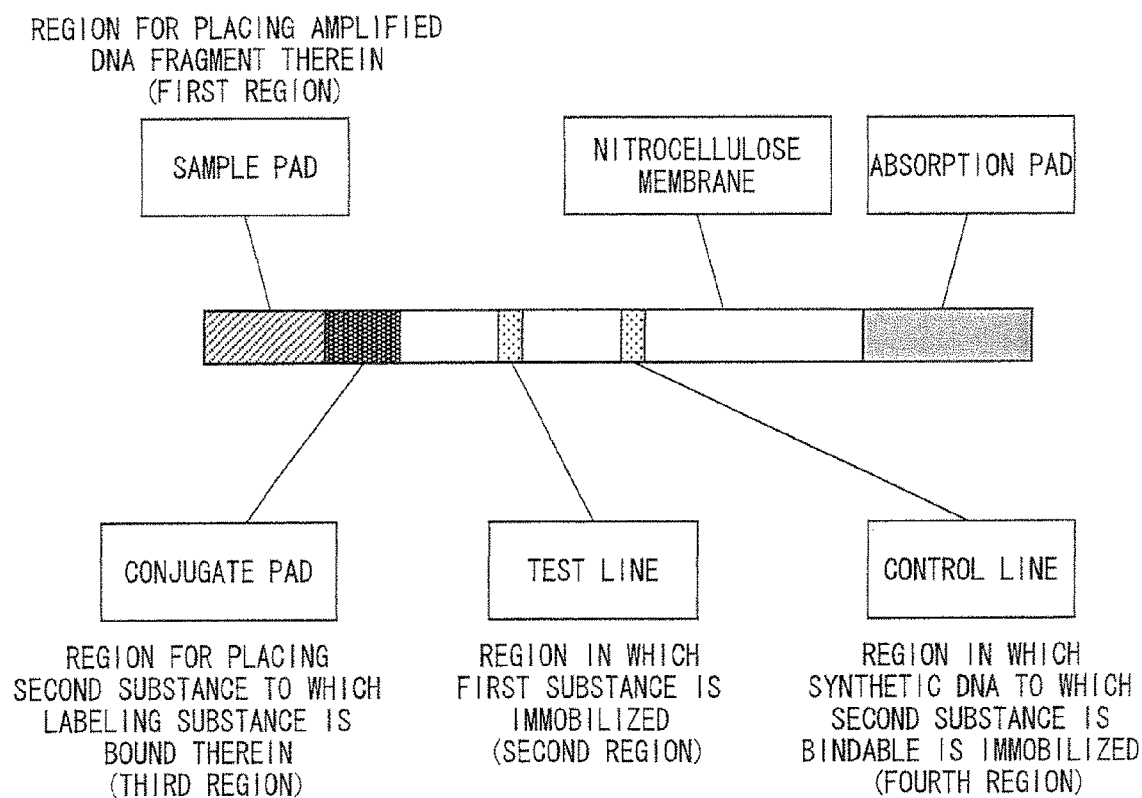
FIG. 3 is a top view showing a stationary-phase medium included in a nucleic acid detection kit in accordance with an embodiment of the present invention.

Further, when embodied as comprising the complex forming step and the amplified DNA concentration step, the nucleic acid detection method of the present invention may be arranged such that both steps are carried out sequentially. Specifically, for example, as illustrated in FIG. 3, the first substance is immobilized to a partial region (see TEST LINE in FIG. 3) of the stationary-phase medium, and on the stationary-phase medium, the amplified DNA fragment (placed to SAMPLE PAD in FIG. 3) and the second substance (placed to CONJUGATE PAD in FIG. 3) to which the labeling substance is bound are respectively placed in separate regions (see SAMPLE PAD and CONJUGATE PAD in FIG. 3), which are different from the region where the first substance is immobilized.

Next, the amplified DNA fragment is diffused, by use of the solvent, toward the region where the second substance to which the labeling substance is bound is placed. Then, the complex is formed in the region where the second substance to which the labeling substance is bound is placed (see CONJUGATE PAD in FIG. 3).

After that, the complex is diffused toward the region where the first substance is immobilized. Then the complex is captured in the region where the first substance is immobilized (see TEST LINE in FIG. 3). With this process, the complex (i.e. the amplified DNA fragment) can be concentrated in the region where the first substance is immobilized.

In such an embodiment, the complex forming step and the amplified DNA fragment concentration step can be carried out sequentially.

After the amplified DNA fragment is concentrated by the method described above, the amplified DNA fragment is detected. As described above, the labeling substance is bound to the amplified DNA fragment. Therefore, the labeling substance is also concentrated as the amplified DNA fragment is concentrated. Any of the labeling substances described above can be detected by a conventionally-known method. The labeling substance is reinforced in signal strength by the concentration.

Accordingly, with the nucleic acid detection method of the present invention, it is possible to detect the amplified DNA fragment highly sensitively.

The method for detecting the labeling substance is not particularly limited, and may be carried out by arbitrarily selecting appropriate means in accordance with the sort of the labeling substance. For example, if the labeling substance is the enzyme or the fluorescent material, the labeling substance can be detected by a detection method conventionally used in the EIA method or a fluorescence immunoassay method (FIA). Further, if the labeling substance is the colored particles, it is possible to detect the labeling substance visually.

Furthermore, even if the amplified DNA fragment does not have the ability to bind to the second substance, and also is not bound to a detectable labeling substance, the amplified DNA fragment may be detected by using, after concentrating the amplified DNA fragment, conventionally-known means for detecting a nucleic acid, such as a nucleic acid stain method.

As described above, with the nucleic acid detection method of the present invention, it is possible to detect a PCR product easily and highly accurately, without requiring any special device.

<II. Nucleic Acid Detection Kit>

A nucleic acid detection kit of the present invention is a nucleic acid detection kit suitably applicable to the operation of the nucleic acid detection method of the present invention, described above. Specifically, the nucleic acid detection kit of the present invention includes at least one of (1) a stationary-phase medium having a first region where the amplified DNA fragment is placed, and second region where the first substance that can specifically bind to the amplified DNA fragment can be immobilized, and (2) a primer having a base sequence that gives the amplified DNA fragment a specific binding ability with respect to the first substance.

Further, in addition to the arrangement described above, the nucleic acid detection kit of the present invention may include (3) a primer having a base sequence that gives the amplified DNA fragment a specific binding ability with respect to the second substance, (4) the first substance, (5) the second substance, and/or (6) the DNA polymerase.

Among these, (2) through (6) are as explained in <I. Nucleic acid detection method>. Accordingly, the detailed explanations of these are omitted here.

Further, the nucleic acid detection kit of the present invention may further include a buffer solution used in the nucleic acid amplification reaction, and various reagents and equipment used in the nucleic acid amplification reaction. A person skilled in the art can easily understand such additions.

The following description deals with (1) the stationary-phase medium described above, more specifically.

[Stationary-phase Medium]

As shown in FIG. 3, the stationary-phase medium only has to include at least (i) the first region (see SAMPLE PAD in FIG. 3) where the amplified DNA fragment is placed, and (ii) the second region (see TEST LINE in FIG. 3) where the first substance that can specifically bind to the amplified DNA fragment can be immobilized.

With the arrangement, the amplified DNA fragment can be concentrated in the second region in such a manner that (i) the first substance is immobilized to the second region, (ii) the amplified DNA fragment is placed in the first region, and (iii) the amplified DNA fragment is diffused by use of the solvent, so as to bind to the first substance in the second region. Note that the second region to which the first substance is immobilized may be referred to as "immobilizing phase".

Further, as shown in FIG. 3, on the stationary-phase medium, it is preferable to further provide a third region (see CONJUGATE PAD in FIG. 3) where the second substance to which the labeling substance is bound is placed. Here, a positional relationship between the first, second, and third regions is not particularly limited, as long as the aforementioned nucleic acid detection method of the present invention can be carried out with the positional relationship. Specifically, the first region, the third region, and the second region may be arranged in this order on a straight line, for example (see FIG. 3). Further, it is preferable that the first and third regions are adjacent to each other.

With the arrangement, the complex is formed in such a manner that (i) the first substance is immobilized to the second region, (ii) the amplified DNA fragment is placed in the first region, (iii) the second substance to which the labeling substance is bound is placed in the third region, (iv) the amplified DNA fragment is diffused by use of the solvent, so as to bind to the second substance to which the labeling substance is bound, in the third region. By further diffusing the complex, the complex and the first substance bind to each other in the second region. This makes it possible to concentrate the amplified DNA fragment in the second region.

Moreover, preferably, the stationary-phase medium, as shown in FIG. 3, further has a fourth region where a nucleic acid fragment that can specifically bind to the second substance can be immobilized. Pointing this case, a positional relationship between the first, second, third, and fourth regions is not particularly limited, as long as the aforementioned nucleic acid detection method of the present invention can be carried out with the positional relationship. Specifically, the first region, the third region, the second region, and the fourth region may be arranged in this order on a straight line, for example (see FIG. 3).

With the arrangement, it becomes possible to immobilize the nucleic acid fragment that can specifically bind to the second substance to the fourth region. Accordingly, by causing the nucleic acid fragment to be immobilized to the fourth region, the second substance to which the labeling substance is bound is diffused from the third region, and binds to the nucleic acid fragment in the fourth region. As a result, the second substance to which the labeling substance is bound is concentrated in the fourth region. After that, it becomes possible to confirm the diffusion of the second substance by detecting the labeling substance thus concentrated.

In other words, with the arrangement, even if the amplified DNA fragment is not detected in the first region, it is possible to easily determine whether the reason why the amplified DNA fragment is not detected is due to nonoccurrence of the diffusion of the amplified DNA fragment, or due to the absence of the amplified DNA fragment (due to the fact that the amplified DNA fragment is not amplified by the PCR).

Note that the nucleic acid fragment that can specifically bind to the second substance is not particularly limited, but may be a DNA fragment that can specifically bind to the second substance, for example. More specifically, for example, the nucleic acid fragment may be the one including the region to which the second substance specifically binds, which region is at an end of the amplified DNA fragment. Further, the nucleic acid fragment may be either a naturally-derived nucleic acid fragment, or a synthesized nucleic acid fragment.

The stationary-phase medium may further has a fifth region (see ABSORBING PAD in FIG. 3) for absorbing a substance which is diffused from the first and third regions, and but not captured in the second and fourth regions, (see FIG. 3). Pointing this case, a positional relationship between the first, second, third, fourth, and fifth regions is not particularly limited, as long as the aforementioned nucleic acid detection method of the present invention can be carried out with the positional relationship. Specifically, for example, the first region, the third region, the second region, the fourth region, and the fifth region may be arranged in this order on a straight line, for example (see FIG. 3).

Further, the first, second, third, fourth, and fifth regions may be arranged either in a horizontal direction or in a vertical direction. Furthermore, the regions may be arranged either in an oblique direction, or in a zigzag pattern.

The stationary-phase medium only has to be capable of diffusing the amplified DNA fragment and the second substance to which the labeling substance is bound, and a material of the stationary-phase medium is not particularly limited. Since the amplified DNA fragment and the second substance to which the labeling substance is bound are generally diffused by use of an aqueous solvent, it is preferable that the stationary-phase medium has a water absorbing substrate.

Further, in the present invention, the amplified DNA fragment is caused to bind to, while being diffused on the stationary-phase medium, (i) the second substance to which the labeling substance is bound, and (ii) the first substance. For this reason, if the water absorbing substrate is significantly low in water-absorbability, the amplified DNA fragment, or the complex constituted by the amplified DNA fragment and the second substance to which the labeling substance is bound tends to become too low in diffusion rate for the measurement to be carried out quickly. On the other hand, if the water absorbing substrate is significantly high in water-absorbability, the amplified DNA fragment becomes too high in diffusion rate to sufficiently bind to the second substance and the first substance. As a result, the detection sensitivity of the amplified DNA fragment tends to become lower.

Therefore, it is preferable to select, as the stationary-phase medium, a water absorbing substrate which can diffuse the amplified DNA fragment in such a diffusion rate that the binding reaction between the amplified DNA fragment and other molecules efficiently occurs.

Specific examples of such a water absorbing substrate encompass: nonwoven fabric; filter paper; glass fiber fabric; a glass filter; a nitrocellulose filter; and a porous material. These water absorbing substrates have an appropriate water absorbing rate, and, for example, if the labeling substance is the colored particles, they are also advantageous in visual confirmation when the colored particles bind to the amplified DNA fragment and then develop a color.

Further, for adjustment of the water absorbability, a surface of the stationary-phase medium may be coated with or immersed in a hydrophilic polymer or a surfactant.

In the stationary-phase medium, all of the first, second, third, fourth, and fifth regions, and the other region may be made from the same material, or may be made from different materials respectively. Further, the stationary-phase medium may be formed such that a substrate made from a certain material is provided as a base, and the first, second, third, fourth, and fifth regions, made either from the same material as that of the substrate, or from a material(s) different from that of the substrate, are provided on the substrate. In this case, each of the regions may be provided on the substrate in any way. For example, the regions may be provided on the substrate in such a manner that a substrate, made either from the same material as that of said substrate, or from the material(s) different from that of said substrate, is attached on said substrate by use of appropriate adhesion means. With such a method, it is possible to obtain a stationary-phase medium having the first, second, third, fourth, and fifth regions, and the other region sequentially.

It is preferable to make the first and third regions, separately from the other regions, from a material which does not prevent the solution containing the amplified DNA fragment, or the solution containing the second substance to which the labeling substance is bound, from moving to the water absorbing substrate. In this case, it is preferable to make the first and third regions from the nonwoven fabric, woven fabric, or the like.

In the stationary-phase medium, a distance between the first and second regions is not particularly limited, as long as the distance allows the amplified DNA fragment to be detected highly sensitively and highly accurately. Specifically, it is preferable that the distance is in a range of 1 cm to 6 cm, more preferably in a range of 3 cm to 4 cm. A distance greater than said range may cause the following problems: (i) the amplified DNA fragment cannot reach the second region, (ii) a detection signal sensitivity becomes too strong, and (iii) it takes a long time for the measurement. On the other hand, the distance shorter than said range may cause the following problems: (i) the labeling substance, which is bound to the amplified DNA fragment concentrated in the second region, cannot develop the color uniformly, and (ii) the detection signal sensitivity becomes too low.

The stationary-phase medium may be in any shape, as long as the shape allows the amplified DNA fragment, and the second substance to which the labeling substance is bound, to be diffused in the stationary-phase medium. More specifically, a rectangular sheet (piece) shape, or a rod shape is suitable for the stationary-phase medium, for example.

Further, in the present invention, the way to immobilize the first substance on the stationary-phase medium (i.e. a method for producing an immobilizing phase) is not particularly limited, and may be a conventionally-known method. Specifically, for example, the physical absorption method, or the covalent bonding method is suitably used as the aforementioned method. Particularly, it is preferable to use the covalent bonding method, as the aforementioned method. With the covalent bonding method, it is possible to bind the first substance onto the stationary-phase medium strongly. Accordingly, it becomes possible to prevent the first substance from dissociating from the stationary-phase medium in use.

Further, in a case where the water absorbing substrate included in the stationary-phase medium does not have any functional group for causing the first substance to bind to the stationary-phase medium by the covalent bonding method, it is possible to (i) manufacture a substrate with a polymer having an appropriate functional group, and (ii) attach the substrate to the water absorbing substrate to such a degree that the water-absorbability of the water absorbing substrate is not suppressed.

Furthermore, the first substance can be immobilized to the stationary-phase medium by (i) applying the solution containing the first substance and the hydrophilic polymer to the water absorbing substrate, and then (ii) immersing the water absorbing substrate in a coagulation solvent for coagulating the hydrophilic polymer. In this case, the hydrophilic polymer may be hydroxypropyl methylcellulose, polyvinyl alcohol, hydroxyethyl cellulose, or the like. Moreover, the coagulation solvent may be acetone, ethanol, methanol, ether, or the like.

Further, on the stationary-phase medium, the nucleic acid fragments that specifically binds to the first and second substances respectively may be immobilized in the first and fourth regions respectively in advance, or may be immobilized by the user himself before the use. Furthermore, it is possible to have an arrangement in which one of the nucleic acid fragments is immobilized in advance, and the other is immobilized by the user himself before the use.

In such an embodiment that the nucleic acid fragments which specifically bind to the first and second substances respectively are not immobilized on the stationary-phase medium in advance, the nucleic acid detection kit of the present invention may include, a reagent or equipment (including the first substance or the nucleic acid fragment) for immobilizing the first substance and the nucleic acid fragments on the stationary-phase medium.

<III. Use of the Present Invention>

The nucleic acid detection method and nucleic acid detection kit of the present invention can be applied to any techniques employing the nucleic acid amplification method. In other words, the nucleic acid detection method and nucleic acid detection kit of the present invention can be applied to techniques in any fields, which techniques encompasses the detection of the amplified DNA fragment (PCR product, for example) by the nucleic acid amplification method.

Specifically, these are applicable to: a research field of the molecular biology; detection of a pathogen; detection of a substance (such as an allergen mixed in a food; livestock management; detection of a nucleotide polymorphism (hereinafter, referred to as "SNP", in some cases); etc.

Accordingly, the present invention may be a method for detecting a pathogen, a method for detecting an impurity (an allergen, for example) in a food, a method for managing livestock, a method for detecting a nucleotide polymorphism, and the like, each of which includes the nucleic acid detection method of the present invention as one step.

Here, the following description deals with the method for detecting a nucleotide polymorphism, the method for detecting a pathogen, and the method for detection an allergen of the present invention, as an embodiment of the use of the present invention, more specifically.

[Nucleotide Polymorphism Detection Method]

First, in the present Specification, "nucleotide polymorphism" indicates that between the individuals, there are two or more sorts of bases at a certain site in a chromosome or in a fragment of the chromosome. In this case, a specific base type is referred to as "wild type", and a base type different from the wild type is referred to as "mutant type". Further, "nucleotide polymorphism site" is a position of the nucleotide polymorphism in which the difference between the wild type and the mutant type exists. Note that in the "nucleotide polymorphism", the one in which a single base is different is called "single nucleotide polymorphisms (SNPs)".

Further, in the present specification, a chromosome including the nucleotide polymorphism site, or a fragment of the chromosome including the nucleotide polymorphism site, each of which has a wild-type base sequence, is called "wild-type nucleic acid" in some cases. Meanwhile, a chromosome including the nucleotide polymorphism site, or a fragment of the chromosome including the nucleotide polymorphism site, each of which has, for example, (1) such a base sequence that in a wild-type nucleic acid, at least one nucleotide (preferably one nucleotide) is point-mutated so as to be substituted by another nucleotide, or (2) such a base sequence that a part of a wild-type nucleic acid has an insertion sequence, a deleted sequence, or the like, is called "mutation-type nucleic acid" in some cases. In the present invention, it is preferable that the mutation-type nucleic acid is such that at least a single base of a wild-type nucleic acid having the nucleotide polymorphism site is substituted by another base.

Further, it is preferable that the mutation-type nucleic acid is known as to which site the nucleotide is mutated (i.e. a mutation site).

In recent years, it has been found that the detection of the nucleotide polymorphism such as the SNP is useful in the medical field, that is, treatment of an illness, prevention of an illness, prognosis of an illness, human constitution evaluation, etc.

Specifically, the nucleotide polymorphism of a gene between individuals is considered as one of the causes of an adverse effect in drug metabolism, and poor outcome of medical treatment due to administration timing and an applied dose of a drug, etc. Therefore, in the field of an antibody drug such as Glivec or Herceptin, the relationship between the nucleotide polymorphism and the poor outcome of medical treatment has been researched.

Further, this nucleotide polymorphism is also known as a cause of a difference among individuals in basal metabolism or the like. Furthermore, it has been suggested that the nucleotide polymorphism is applicable to determination of an obesity type, a skin type, etc. In addition to these, it is expected that the nucleotide polymorphism can be used as a genetic marker for a great number of illnesses.

Therefore, such analysis of the nucleotide polymorphism is clinically important, and routine phenotype classification is particularly recommended for a clinical research targeting a psychiatric patient and a person who want to kill himself (see Gram and Brsen, European Consensus Conference on Pharmacogenetics. Commission of the European Communities, Luxembourg, p87-96 (1990); Balant et al., Eur. J. Clin. Pharmacol. Vol. 36, from p551 to p554 (1989)).

For the reasons set forth above, the identification of the nucleotide polymorphism site of the mutated gene, which is to become the cause, and development of the subsequent analysis method of each nucleotide polymorphism have been demanded.

A conventional technique for analyzing the nucleotide polymorphism is, for example, a nucleic acid sequence determination method. The nucleic acid sequence determination method can detect and identify the nucleotide polymorphism included in the nucleic acid sequence. However, it includes preparation of a template nucleic acid, a DNA polymerase reaction, polyacrylamide gel electrophoresis, analysis of a nucleic acid sequence, and the like, so that it requires a great amount of effort and time.

Further, although the nucleic acid sequence determination method can realize power saving to a certain degree by use of a recent automatic sequencer, such a device is expensive.

In order to solve the problems described above, an SNP detection method using the PCR has been developed in recent years (see Japanese Patent Application Publication, Tokukaisho, No. 61-274697 A (1986) (Publication Date: Dec. 4, 1986), and Japanese Patent Application Publication, Tokukaisho, No. 62-281 A (1987) (Publication Date: Jan. 6, 1987)).

In this method, as one of two primers used in the gene amplification method, a wild-type primer and a mutation-type primer are used wherein the wild-type primer is completely complementary with respect to an end region of the amplified region of the wild-type gene, and the mutation-type primer is completely complementary with respect to an end region of the amplified region of the mutation-type gene.

The mutation-type primer is designed such that its 3' end is to be a nucleotide complementary with respect to a nucleotide of the anticipated nucleotide polymorphism site. By using the wild-type primer and the mutation-type primer independently, a gene sample is subjected to the gene amplification method. Here, in the case of a wild-type gene sample, the nucleic acid is amplified with the wild-type primer. Meanwhile, if the mutation-type primer is used, since the 3' end of the mutation-type primer is not complementary with respect to the corresponding nucleotide of the gene sample (mismatch), the elongation reaction would not occur and the nucleic acid would not be amplified.

On the other hand, in a case of a mutation-type gene sample, the nucleic acid is not amplified with the wild-type primer, but amplified with the mutation-type primer.

Accordingly, in a case where each of the wild-type primer and the mutation-type primer is used, it is possible to determine weather the gene sample is the wild type or the mutation type by checking whether or not the nucleic acid is amplified. That is, the nucleotide polymorphism in the gene sample can be detected by the determination.

In Japanese Patent Application Publication, Tokukaisho, No. 61-274697, it is checked, by the hybridization using a probe which can specifically bind to the nucleic acid, whether or not the nucleic acid is amplified. On the other hand, in Japanese Patent Application Publication, Tokukaisho, No. 62-281, it is checked, by separating the nucleic acid by the electrophoresis, and then dyeing it with ethidium bromide, whether or not the nucleic acid is amplified.

Further, as the SNP detection method using the PCR, an Invader method, a TaqMan method, etc. have been known.

Furthermore, other than the method using the PCR, a method employing a DNA chip or a DNA array has been proposed as the SNP detection method, for example. Specifically, for example, in the method employing the DNA array, the SNP can be detected by (i) arraying a great number of probe DNA densely on a solid phase substrate, and (ii) causing DNA sample and the probe DNA to hybridize with each other on the solid phase surface.

However, the SNP detection methods disclosed in Tokukaisho 61-274697 and Tokukaisho 62-281 require confirming, after amplifying the gene sample by the PCR, the amplified product by the electrophoresis, or, in some cases, require confirming the amplified product by additional hybridization. Therefore, the methods are time-consuming and inefficient.

Further, a method called "Invader method", or a method called "TaqMan method" requires an extra expensive fluorescent primer, or an extra expensive device for detecting fluorescence of the amplified product of the gene sample. In addition to the problem, the Invader method or the TaqMan method has another problem of complicated operation due to the necessity of an enzyme reaction other than the PCR.

Moreover, in the method employing the DNA chip or the DNA array, the hybridization between the probe DNA on the solid phase surface and the DNA sample is carried out. This requires a long reaction time period, and causes a problem of low efficiency. Further, the single nucleotide polymorphism substantially does not vary in Tm value, so that it is impossible to detect the mismatch highly accurately. Furthermore, this method requires an expensive device and troublesome operation in the similar manner to the Invader method and the TaqMan method, each of which uses the PCR.

On the other hand, the nucleotide polymorphism detection method of the present invention includes the nucleic acid detection method of the present invention as one step, so that it is possible to detect the nucleotide polymorphism easily and highly accurately without requiring any special device.

Accordingly, if the detection target is the nucleotide polymorphism whose relationship with an onset of an illness or a body constitution has been found, it is possible to obtain, by the nucleotide polymorphism detection method of the present invention, data for carrying out treatment of the illness, prevention of the illness, prognosis of the illness, or body constitution evaluation.

Figure 4:
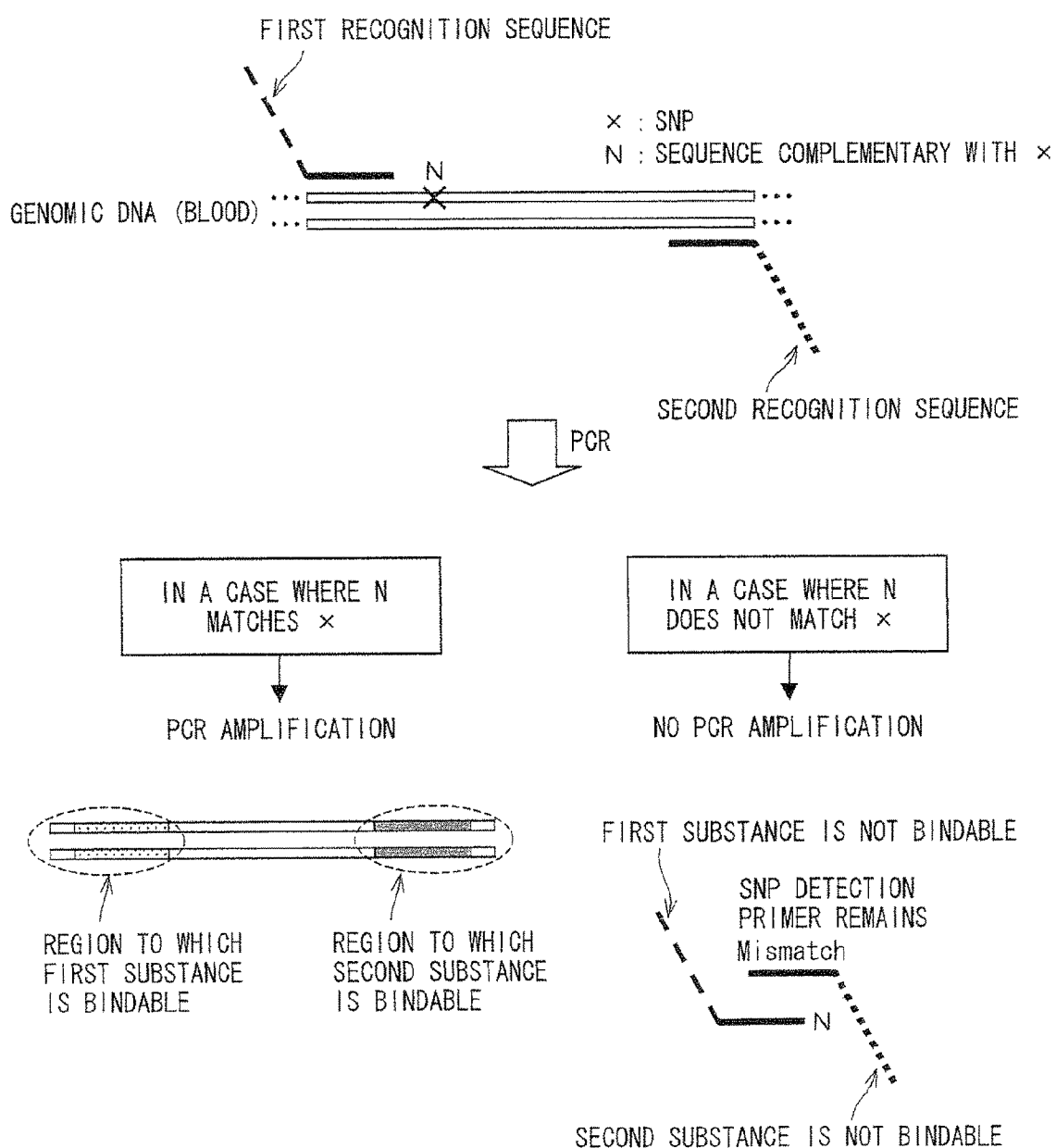
FIG. 4 is a view showing an embodiment of the use of the nucleic acid detection method in accordance with the embodiment of the present invention.

Here, the following description deals with the nucleotide polymorphism detection method of the present invention more specifically, with reference to FIG. 4.

First, in the nucleotide polymorphism detection method of the present invention, the DNA sample is the one having the nucleotide polymorphism site. Generally, it is preferable to use a DNA sample having the nucleotide polymorphism site of a gene whose relationship with an illness, a body constitution, metabolism, secretion, differentiation, an acceptor, or the like is known. Specifically, for example, the DNA sample may have the nucleotide polymorphism site of a gene such as (i) cytochrome P450 (CYP) genes such as: CYP2C9 (which is related to metabolism of phenitoin, warfarin, tolbutamide, and NSAID); CYP2C18 (which is related to metabolism of diazepam); CYP2C19 (which is related to metabolism of omeprazole, diazepam, and the like); CYP26D (which is related to metabolism of amitriptyline, and the like); and CYP2A6 (which is related to metabolism of coumarin, and nicotine), (ii) genes such as: thiopurine methyltransferase (TPMT); N-acetyltransferase (NAT); aldehyde dehydrogenase (ALDH); cholesterol ester transfer proteins (CETP); angiotensin-converting enzyme (ACE); β2 agonist receptor ((β2AR); mitochondria A1555G; a ryanodin receptor; and a peroxisome proliferator-activating receptor, and (iii) genes related to a long QT syndrome (such as a LQT1 gene, and a LQT2 gene). Specifically, for example, such a DNA sample may be blood or a solution having genome DNA isolated from the blood.

Further, in the PCR step described above, the PCR is carried out by using at least one of: a primer set for detecting the mutation-type nucleic acid; and a primer set for detecting the wild-type nucleic acid.

In view of the detection accuracy, it is preferable to carry out the PCR by using each of the primer set for detecting the mutation-type nucleic acid, and the primer set for detecting the wild-type nucleic acid. The following description explains this more specifically. As the nucleotide polymorphism, there are three types, that is: (i) neither of a pair of genes has the nucleotide polymorphism (wt/wt); (ii) a case where one of the pair of genes has the nucleotide polymorphism (mt/wt); and (iii) a case where among both of the pair of genes have the nucleotide polymorphism (mt/mt). Here, "wt" indicates the wild type, and "mt" indicates the mutation type. In the case of the mt/wt type, the amplified DNA fragment (PCR product) is generated by use of either the primer set for detecting the mutation-type nucleic acid, or the primer set for detecting the wild-type nucleic acid.

Therefore, if the PCR is carried out by using the two primer sets independently, it becomes possible to determine whether the genes (i) have the mutation-type in a homo relationship, (ii) have the mutation-type in a hetero relationship, or (iii) has no mutation-type.

Each of the two primer sets described above has two primers (that is, a forward primer and a reverse primer). As to the two primers, it is preferable that the two primer sets are identical in one of the two primers, and are different from each other in the other one of the two primers in base sequence, so as to make it possible to specifically detect the mutation-type nucleic acid or the wild-type nucleic acid. Note that the primer identical in base sequence (hereinafter, referred to as "common primer" in some cases) is a primer which binds to a base sequence preserved in both the wild-type nucleic acid and the mutation-type nucleic acid. Further, in such an embodiment, it is preferable that the primers which are different from each other in base sequence (hereinafter, referred to as "primer for detecting the wild type" and "primer for detecting the mutation type" in some cases) are identical with each other in length.

Furthermore, each of the primer for detecting the wild type and the primer for detecting the mutation type may be the forward primer or the reverse primer. That is, it is possible that (i) both the primer for detecting the wild type and the primer for detecting the mutation type are the forward primers, and the common primer is the reverse primer, or (ii) both the primer for detecting the wild type and the primer for detecting the mutation type are the reverse primers, and the common primer is the forward primer. Note that FIG. 4 shows the case where the primer for detecting the mutation type is the forward primer, and the common primer is the reverse primer.

Moreover, each of the primer for detecting the wild type and the primer for detecting the mutation type includes the template binding sequence, as explained in <I. Nucleic acid detection method>, and may further include the first recognition sequence and/or the second recognition sequence. The first and second recognition sequences are explained in the above description, so that the explanations of these are omitted here.

The template binding sequence of the primer for detecting the wild type and the primer for detecting the mutation type is designed to include the base (base sequence) of the nucleotide polymorphism site in the DNA sample. More specifically, in a case where the nucleotide polymorphism to be detected is the single nucleotide polymorphism, the nucleotide polymorphism detection method of the present invention detects a difference of a single nucleotide. That is, the nucleotide polymorphism site is constituted by a single base.

In such an embodiment, the template binding sequence is designed such that the 3' end of the template binding sequence in each of the primer for detecting the wild type and the primer for detecting the mutation type, preferably the 3' end of each of the primers, becomes the base of the nucleotide polymorphism site (in the case of the primer for detecting the mutation type, the base of the nucleotide polymorphism site of the mutation-type nucleic acid; and in the case of the primer for detecting the wild type, the base of the nucleotide polymorphism site of the wild-type nucleic acid). Note that FIG. 4 schematically shows the primer for detecting the mutation type (see FIRST PRIMER in FIG. 4).

Further, either in the primer for detecting the wild-type or in the primer for detecting the mutation type, it is preferable to design an entire region which binds to the template to have a length in a range of 15 bases to 30 bases, more preferably in a range of 18 bases to 25 bases. That is, it is preferable that the region is such that the base of the nucleotide polymorphism site (in the case of the primer for detecting the mutation-type nucleic acid, the base of the nucleotide polymorphism site of the mutation-type nucleic acid; in the case of the primer for detecting the wild-type nucleic acid, the base of the nucleotide polymorphism site of the wild-type nucleic acid) is the 3' end, and 15 bases to 30 bases (more preferably 18 bases to 25 bases) complementary with respect to the DNA sample are arranged in a direction toward the 5' end.

Further, it is preferable to add the first and/or second recognition sequences closer to the 5' end than the 15 bases to 30 bases complementary with respect to the DNA sample.

Furthermore, the common primer also has the template binding sequence, and may further have the first and/or second recognition sequence.

In the common primer, (i) the template binding sequence is used in combination with the primer for detecting the mutation type or the primer for detecting the wild type, based on the base sequence of the region which is to be amplified by the PCR with respect to the DNA sample, and (ii) the template binding sequence is selected so that in a case where the PCR is carried out, the desired amplified DNA fragment (PCR product) can be obtained. The length of the template binding sequence of the common primer is not particularly limited, but generally, it is preferable to design the template binding sequence to have a length in a range of 15 bases to 30 bases, more preferably in a range of 18 bases to 25 bases. Further, it is preferable to design the common primer so that the amplified DNA fragment has a length in a range of 50 bp to 500 bp.

With the method described above, by designing the primer for detecting the mutation type, the primer for detecting the wild type, and the common primer, it becomes possible to design each of the primer set for detecting the mutation-type nucleic acid, and the primer set for detecting the wild-type nucleic acid.

The following describes the case where the PCR is carried out with the use of such primer sets. In a case where the DNA sample has the wild-type, the amplified DNA fragment (PCR product) can be obtained by the PCR using the primer set for detecting the wild-type nucleic acid, but no amplified DNA fragment can be obtained by the PCR using the primer set for detecting the mutation-type nucleic acid.

On the other hand, in a case where the DNA sample has the mutation-type, as shown in FIG. 4, no amplified DNA fragment (PCR product) can be obtained by the PCR using the primer set for detecting the wild-type nucleic acid, but the amplified DNA fragment can be obtained by the PCR using the primer set for detecting the mutation-type nucleic acid.

Each of the primer sets described above includes the primer having the first and/or second recognition sequences so that it is possible to easily detect, by the nucleic acid detection method of the present invention, whether or not the amplified DNA fragment is obtained.

Note that here, the embodiment describes a case where the two sorts of base type, that is, the wild type and the mutation type, are detected. However, if the mutation-type is constituted by a plurality of mutation types, it is also possible to determine the base type of the DNA sample by designing a plurality of primer sets in accordance with the number of the mutation types, based on the same principle.

Thus, in accordance with the nucleic acid detection method of the present invention, it is possible to detect the nucleotide polymorphism easily and highly accurately without requiring any special device.

[Pathogen Detection Method]

A pathogen detection method of the present invention only has to include a step for detecting, by use of the nucleic acid detection method of the present invention, a gene specifically included in a pathogen.

Specifically, for example, the pathogen may be, but not particularly limited to, a pathogenic bacterium, a pathogenic virus, a food-poisoning bacterium, a bacterium causing hospital infection, a virus causing hospital infection, or the like.

More specifically, for example, the pathogen may be (i) a virus such as a hepatitis C virus (HCV), a cytomegalovirus (CMV), an Epstein-Barr virus (EBV), a herpesvirus, or a human immunodeficiency virus (HIV), (ii) a bacterium such as an *Escherichia coli* bacterium (O157, for example), a tuberculosis bacterium, a typhoid bacterium, a *salmonella* bacterium, or a *vibrio parahaemolyticus* bacterium, or (iii) a microorganism such as a mycoplasma.

The following description deals with the pathogen detection method of the present invention more specifically. For example, the pathogen detection method of the present invention employs the nucleic acid detection method described above so as to determine whether or not the DNA sample, prepared from a sample which is the target of the detection as to the presence or absence of the pathogen, includes the gene specifically included in the pathogen. As a result, if such a gene is detected, it is determined that the sample contains the pathogen.

This makes it possible to determine whether or not the sample contains the pathogen easily and highly accurately without requiring any special device. That is, the pathogen detection method of the present invention is applicable to diagnosis of communicable diseases of microorganisms.

[Allergen Detection Method]

An allergen detection method of the present invention only has to include a step for detecting, by use of the nucleic acid detection method of the present invention, a gene encoding an allergen.

Specifically, for example, the allergen may be, but not particularly limited to, an allergen included in a food. More specifically, the allergen may be an albumen allergen, a milk allergen, a wheat allergen, a buckwheat allergen, or a peanut allergen, for example.

The following description deals with the allergen detection method of the present invention more specifically. For example, the allergen detection method of the present invention employs the nucleic acid detection method described above so as to determine whether or not the DNA sample prepared from a food contains a gene encoding an egg allergen, a milk allergen, a wheat allergen, a buckwheat allergen, a peanut allergen, or the like. As a result, if such a gene is detected, it is determined that the food contains a material containing such an allergen.

This makes it possible to determine whether or not a sample such as a food contains a material containing an allergen, easily and highly accurately without requiring any special device. Note that the derivation of an allergen is not limited to those described above. For example, in a case of grain, the derivation of the allergen includes all of the followings: rice; mais; Italian millet; proso millet; Japanese millet; buckwheat; and pulses.

Further, DNA is stable against heat, and can be detected in small amounts even in a manufactured food. Accordingly, data obtained by the allergen detection method of the present invention can be used not only for food labeling, or allergen information of a food, but also for detection of a residual food additive in small amounts such as a processing material or a carry-over, or detection of a mixed substance that is not intended by a manufacturer, such as the presence or absence of mutual contamination between the manufacturing lines.

Other than these, the present invention is applicable to determination of parentage of a mammal including a human, identification of a pedigree of livestock, identification of a breed of an agricultural product, etc. Specifically, for example, in the case of livestock, the present invention is applicable to: pedigree registration; individual recognition; parentage determination; removal of an individual carrier of a disease-causing gene; etc.

Note that the present invention is not limited to the descriptions of the embodiments above, but may be altered by a skilled person within the scope of the claims. An embodiment based on a proper combination of technical means disclosed in different embodiments is encompassed in the technical scope of the present invention.

EXAMPLES

The following description explains the present invention based on the examples more specifically. However, the present invention is not limited to these. A person skilled in the art can change, modify, or alter the present invention in various ways within the scope of the present invention.

Example 1

Production of PCR Amplified Product (1) Template DNA and Primer
As a template, pUC19 (manufactured by TaKaRa Bio Co.) was used, and the following primer E1 and primer B1 were designed so as to obtain 100 base pairs by PCR amplification.
Primer E1: 5'-gctcgaattcactggccgtcg-3' (shown in SEQ ID NO: 1)
Primer B1: 5-ctatggatcctacgccagctggcgaaaggg-3' (shown in SEQ ID NO: 2)

The primer E1 was designed such that in the sequence, an EcoRI methylase recognition sequence "GAATTC" exists from the 5th base to the 10th base from a 5' end. Further, the primer B1 was designed such that in the sequence, a BamHI methylase recognition sequence "GGATCC" exists from the 5th base to the 10th base from a 5' end.

Furthermore, in the downstream of the EcoRI methylase recognition sequence of the primer E1, a sequence of 11 bases that correspond to the pUC19 was designed. In the similar manner, in the downstream of the BamHI methylase recognition sequence of the primer B1, a sequence of 20 bases that correspond to the pUC was designed. After that, based on the sequences thus designed, synthetic oligonucleotide was synthesized.

By use of the primer E1 and the primer B1 thus obtained, the PCR was carried out, so as to produce an amplified DNA product constituted by 100 base pairs.

(2) PCR
Into a PCR tube having a capacitor of 0.2 ml, 10 pmol of the primer E1, 10 pmol of the primer B1, and 10 ng of the pUC19 were provided, so that 20 tubes each of which contains a 50 µl PCR reaction solution were prepared in accordance with instructions of an ExTaq PCR kit (manufactured by TaKaRa Bio Co.).

After that, the PCR tube was set in a PCR thermal cycler (GeneAmp PCR System, manufactured by Applied Biosystems Inc.), where after being subjected to heat treatment at a temperature of 95° C. for 5 minutes, the PCR reaction solution was subjected to the following PCR cycle 35 times: (1) at 95° C. for 30 seconds, (2) at 55° C. for 30 seconds, (3) at 55° C. for 30 seconds, and then (4) at 74° C. for 30 seconds. As a result, target 100 base pairs were amplified.

The PCR reaction solution thus obtained was subjected to electrophoresis, and then the primers were removed from the PCR reaction solution by use of Suprec 01 (manufactured by TaKaRa Bio Co.). Here, the operation was carried out in accordance with the protocol attached to Suprec 01.

As a result, a amplified PCR product (approximately 200 µg) constituted by 100 base pairs was obtained, which amplified PCR product has the EcoRI methylase recognition sequence, and the BamHI methylase recognition sequence. Note that hereinafter, this amplified fragment is referred to as "EB100".

Example 2

Detection of PCR Amplified Product (1) Production of Colloidal Gold Labeled EcoRI Methylase
To 8.0 ml of a colloidal gold solution (10 nm colloidal gold particle diameter, manufactured by GE Healthcare Co.), 30 µl of $0.2M K_2CO_2$ was added, so that the colloidal gold solution had a pH of 7.6. Then 500 units of a commercially-available EcoRI methylase (manufactured by NEB Co.) were added to the colloidal gold solution. After that, the resultant was agitated at a room temperature for 10 minutes, and 40 µl of a 0.1% PEG 6000 solution was added to the resultant. Then the resultant was agitated for 10 minutes, and after that, the resultant thus obtained was subjected to centrifugation at a temperature of 4° C. at 15,000 rpm for 60 minutes.

To the deposition thus obtained, 4.0 ml of 0.3% BSA and 0.25% PEG6000-containing 0.1M Tris buffer solution (pH 7.6) was added, and then the deposition was uniformly suspended. After that, the resultant was subjected to the centrifugation at 15.000 rpm for 60 minutes. Then, similar washing operation was carried out twice, and after that, to the deposition thus obtained, 0.8 ml of 0.3% BSA, 0.25% PEG6000, 4% sucrose and 0.1% $NaN_3$-containing 0.1M Tris buffer solution (pH 7.6) was added. Then the resultant was uniformly suspended. As a result, a colloidal gold labeled EcoRI methylase solution was obtained.

(2) Production of Detection Piece
To a position 30 mm away from an end of a nitrocellulose membrane (8 µm pore diameter, 6 mm×60 mm, manufactured by GE Healthcare Co.), 500 units of a BamHI methylase (in the 0.1M Tris buffer solution (pH7.6), manufactured by NEB Co.) was applied in a line by use of a dispenser, so as to produce a test line (second region).

This membrane was immersed in a solution containing 1% by weight bovine serum albumin and 0.1% by weight polyoxyethylene (10) octylphenyl ether (manufactured by Wako Pure Chemical Industries, Ltd.) for 10 minutes, and then was dried at a temperature of 40° C. for 2 hours. Next, to a backside of the membrane (opposite side of the enzyme applied surface), a polyester film (100 μm thickness) was attached by use of spray glue. Further, filter paper for chromatography (6 mm×8 mm, 3 mm, thickness, manufactured by Advantec Toyo Kaisya, Ltd.) were attached to positions 0 mm to 5 m away from both ends of the membrane, respectively. As a result, a detection piece (stationary-phase medium) was produced. Note that one of the filter paper for chromatography was a sample pad (first region) where an amplified PCR product-colloidal gold complex was to be placed, and the other was an absorption pad (fifth region) for absorbing an unreacted complex.

(3) Detection of PCR Amplified Product

The EB100 solution prepared in Example 1, a 0.9% by weight NaCl-containing 0.1M Tris buffer solution (pH 7.6), and the colloidal gold labeled EcoRI methylase solution produced in the above (1) were mixed together so as to prepare a test sample. Note that the test sample was prepared such that the solid content concentration was approximately 0.02% by weight, and the amount of the EB 100 in 60 μl of the test sample was set to be each of: 1 μg; 10 μg; and 100 μg.

To the filter paper for chromatography of the detection piece produced in the above (2), 60 μl of the test sample was dripped. After 30 minutes passed since the mixed solution was developed to the detection piece, it was observed visually whether or not there was color development on the test line on the detection piece. Table 1 shows the result. Note that Table 1 also shows the result of similar operation using not the EB100 solution but the colloidal gold labeled EcoRI methylase solution only, as a comparison.

TABLE 1

| | EB100 amount (μg) | | | |
|---|---|---|---|---|
| | 0 | 1 | 10 | 100 |
| EB100 solution | − | − | + | − |
| Only colloidal gold labeled EcoRI methylase | − | − | − | − |

As described above, in the nucleic acid detection method of the present invention, the amplified DNA fragment having the first substance binding site to which the first substance can specifically bind is concentrated by use of the first substance. Therefore, it becomes possible to detect the amplified double-stranded DNA fragment amplified by the nucleic acid amplification method, easily and highly accurately without requiring any special device.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

Industrial Applicability

As described above, with the present invention, with the use of an affinity tag formed to an amplified DNA fragment amplified by a nucleic acid amplification method, the amplified DNA fragment is concentrated and detected. Therefore, it becomes possible to detect the amplified DNA fragment amplified by the nucleic acid amplification method, easily and highly accurately without requiring any special device. For this reason, the present invention is widely applicable to any industrial fields making use of a nucleic acid amplification method (the PCR, for example), such as: a basic research field such as molecular biology; a medical field; a food field; a public health field; an environment field; a pharmaceutical field; and an agriculture, and forestry and fisheries field.

The invention claimed is:

1. A nucleic acid detection method for detecting an amplified double-stranded DNA fragment amplified by a nucleic acid amplification method, wherein:
   the amplified DNA fragment has a first substance binding site to which the first substance is specifically bindable; and
   the nucleic acid detection method comprises the step of:
   concentrating the amplified DNA fragment by causing the amplified DNA fragment to bind to the first substance;
   wherein the amplified DNA fragment further has a second substance binding site to which the second substance is specifically bindable; and
   said step of concentrating including:
   (i) forming a complex by binding the amplified DNA fragment to the second substance to which a labeling substance is bound, and
   (ii) binding the complex to the first substance; and
   wherein the amplified DNA fragment is a double-stranded DNA fragment obtained by the nucleic acid amplification method by use of two primers;
   one of the two primers has a base sequence to which the first substance is bindable in a double strand formed by binding the one of the two primers to a complementary strand; and
   the other one of the two primers has a base sequence to which the second substance is bindable in a double strand formed by binding the other one of the two primers to a complementary strand; and
   said step of concentrating further including:
   (i) on a stationary-phase medium to which the first substance is immobilized, placing the amplified DNA fragment in a first region, and placing the second substance to which the labeling substance is bound in a third region, the first region and third region being different from each other and being different from a second region in which the first substance is immobilized,
   (ii) diffusing the amplified DNA fragment by use of a solvent to the third region,
   (iii) forming a complex in the third region by binding the amplified DNA fragment to the second substance to which the labeling substance is bound,
   (iv) diffusing the complex on the stationary-phase medium to the second region by use of the solvent, and
   (v) binding the first substance and the complex to each other in the second region; and
   wherein the stationary-phase medium further has a fourth region where a nucleic acid fragment that can specifically bind to the second substance can be immobilized; and
   the second substance to which the labeling substance is bound and which is diffused from a region for placing the second substance to which the labeling substance is bound binds to the nucleic acid fragment in the fourth region; and
   wherein the first substance and the second substance are each a methylase.

2. The nucleic acid detection method as set forth in claim 1, wherein:
   the first substance and the second substance are different from each other.

* * * * *